(12) United States Patent
Kesling (10) Patent No.: US 8,029,275 B2
(45) Date of Patent: Oct. 4, 2011

(54) SELF-LIGATING ORTHODONTIC BRACKET

(75) Inventor: Andrew C. Kesling, Lakeside, MI (US)

(73) Assignee: TP Orthodontics, Inc., Westville, IN (US)

( * ) Notice: Subject to any disclaimer, the term of this patent is extended or adjusted under 35 U.S.C. 154(b) by 161 days.

(21) Appl. No.: 12/387,265

(22) Filed: Apr. 30, 2009

(65) Prior Publication Data

US 2010/0279247 A1    Nov. 4, 2010

(51) Int. Cl.
*A61C 3/00* (2006.01)
(52) U.S. Cl. .......................................................... 433/10
(58) Field of Classification Search .................. 433/8–17
See application file for complete search history.

(56) References Cited

U.S. PATENT DOCUMENTS

| | | | |
|---|---|---|---|
| 4,842,514 A | 6/1989 | Kesling | |
| 4,877,398 A | 10/1989 | Kesling | |
| 5,125,832 A | 6/1992 | Kesling | |
| 5,224,858 A | 7/1993 | Hanson | |
| 5,474,445 A | 12/1995 | Voudouris | |
| 5,711,666 A | 1/1998 | Hanson | |
| 6,168,429 B1 * | 1/2001 | Brown | ............................ 433/11 |
| 6,257,883 B1 | 7/2001 | Voudouris | |
| 6,554,612 B2 | 4/2003 | Georgakis et al. | |
| 6,582,226 B2 | 6/2003 | Jordan et al. | |
| 6,659,767 B2 | 12/2003 | Abels et al. | |
| 6,682,345 B2 | 1/2004 | Kesling et al. | |
| 6,685,468 B1 | 2/2004 | Kesling | |
| 7,025,591 B1 | 4/2006 | Kesling | |
| 7,264,468 B1 | 9/2007 | Kesling et al. | |
| 2007/0248928 A1 * | 10/2007 | Damon | ............................ 433/10 |

OTHER PUBLICATIONS

Kidney-shaped. (n. d.) Collins English Dictionary—Complete and Unabridged. (1991, 1994, 1998, 2000, 2003). Retrieved Nov. 30 2010 from http://www.thefreedictionary.com/kidney-shaped.*

* cited by examiner

*Primary Examiner* — Cris L Rodriguez
*Assistant Examiner* — Heidi M Eide
(74) *Attorney, Agent, or Firm* — Lloyd L. Zickert

(57) ABSTRACT

A self-ligating orthodontic bracket including a base mountable on a tooth and having upstanding hinge members with aligned slots defining an archwire slot and for pivotally and slidably receiving a pair of openable and closable jaws and a spring member engaging said jaws and actuable upon opening and closing said jaws to selectively lock the jaws into open position for insertion or removal of an archwire and closed position for locking the archwire to the bracket.

9 Claims, 6 Drawing Sheets

SELF-LIGATING ORTHODONTIC BRACKET

This invention relates in general to an orthodontic appliance for connecting an archwire to a tooth, and more particularly to a self-ligating orthodontic bracket mountable on a tooth that may be selectively opened for insertion or removal of an archwire or closed for retaining an archwire in the bracket, and still more particularly to a self-ligating orthodontic bracket having a pair of slidable and pivotally mounted jaws selectively locked in open or closed positions by a spring member.

BACKGROUND OF THE INVENTION

Heretofore, it has been well known to provide self-ligating orthodontic brackets for use in the orthodontic treatment of patients that eliminate the need to rely on ligatures for retaining an archwire in the archwire slot of the bracket. A self-ligating bracket is intended to enhance the efficiency of orthodontic treatment and to eliminate any problem encountered in ligature failure whether the ligature be elastomeric or wire in form.

The orthodontic bracket of the invention is an improvement over the double jaw bracket disclosed in U.S. Pat. No. 7,025,591 wherein the bracket of the invention improves archwire control as well as functional operability.

Further, it has been known to provide self-ligating brackets that will release the archwire from the slot whenever the forces on an archwire exceed a predetermined minimum value, such as disclosed in U.S. Pat. Nos. 6,554,612 and 6,582,226.

Another example of a self-ligating bracket having a ligating latch spring member is disclosed in U.S. Pat. No. 5,711,666.

Moreover, some heretofore known self-ligating brackets are burdened by complex mechanical configurations that have a tendency to excessively trap food particles, irritate the tissues of the mouth, and impose difficulty in opening and closing procedures.

Heretofore, it has also been well known to provide self-ligating orthodontic brackets for performing edgewise techniques when using an edgewise archwire in a rectangular slot as in above-noted U.S. Pat. No. 7,025,591, but not in performing the Tip-Edge technique.

It has also been known to provide brackets to perform the Tip-Edge technique as in U.S. Pat. Nos. 4,877,398 and 5,125,832, both with and without the uprighting wire feature as disclosed in U.S. Pat. No. 6,682,345, but it has not been known to provide a self-ligating bracket to perform the Tip-Edge technique with the uprighting feature.

It also has been known to provide an edgewise bracket for receiving an edgewise wire and for performing an edgewise technique that includes an uprighting tunnel, as in U.S. Pat. No. 7,264,468.

SUMMARY OF THE INVENTION

The self-ligating orthodontic appliance of the present invention relates primarily to a bracket in one configuration for coacting with a main archwire to perform the edgewise technique and in another configuration to perform the Tip-Edge technique. Both of these techniques are well known in the field of orthodontically treating patients. While brackets configured to perform the edgewise technique would normally receive a generally rectangular in cross section archwire to apply tip, torque, rotational and in/out compensation functions, it should be appreciated that such a bracket can be used in one stage of treatment with a round wire. It is known that a rectangular archwire is nearly always used in the later stages of treatment.

Similarly, a bracket that includes a Tip-Edge slot for performing the Tip-Edge technique like in U.S. Pat. No. 6,682,345 which can perform crown tipping, limit root uprighting and torquing functions, may be used with either rectangular or round wire. Such brackets are made and sold by TP Orthodontics, Inc. of Westville, Ind. (TP) under the registered trademark TIP-EDGE, also owned by TP Orthodontics, Inc. Again, it is normal to use rectangular wire in a Tip-Edge slot in the later stages of orthodontic treatment.

In either the edgewise or Tip-Edge version of the bracket of the present invention, the bracket may also be configured to include vertical slots for receiving the anchoring end of uprighting springs or horizontal slots for receiving an uprighting wire that would also be threaded through other brackets.

It should also be appreciated that the bracket of the invention may be made of metal, ceramic, plastic or any suitable material that can be employed for making acceptable brackets. Further, the bracket of the invention for performing an edgewise technique may be understood to be configured for any suitable prescription known in the orthodontic field, such as the McLaughlin Bennett Trevisi system, the Roth system, the Andrews system, the Ricketts system, or any other system that is known.

The self-ligating bracket of the invention includes a base that is provided with a tooth mounting face for direct mounting on a tooth or for receiving a moldable resin base that in turn is bonded directly to a tooth. The bracket base includes a pair of upstanding and generally parallel hinge members having archwire slot formations, which hinge members are interconnected by a plate. A pair of jaws is pivotally and slidably connected to the hinge members which function to open and close the archwire slot of the bracket to permit insertion or withdrawal of an archwire when in the open position and retention of an archwire in the closed position. Kidney-shaped openings on the jaws engage hinge pins held by the upstanding members and coact with a spring member mounted on the jaws to pivotally and slidably move to selectively lock the jaws selectively in open or closed positions. The spring member also serves as a floor for the archwire when the jaws are in closed and locked position.

As above noted, the base may be provided with a mounting pad in the form of cured plastic material of a suitable polymer resin as disclosed in U.S. Pat. No. 6,685,468 to not only enable the bracket to be bonded to a tooth with a suitable bonding material but also to be easily removed when the bracket has exhausted its function in the treatment procedure. A foil/mesh bonding pad may also be attached to the base to allow bonding of the bracket to a tooth. Further, it should also be appreciated that a band may be attached to the base for banding the bracket to a tooth.

Where the bracket may be provided with a polymer resin bonding pad, it may also include an uncured light or chemical curable layer of polymer resin and shipped by the manufacturer to a user so that it may be directly mounted onto a tooth and thereafter the uncured layer may be cured to suitably bond the bracket to a tooth.

Moreover, it will be appreciated that the archwire slot of the edgewise or Tip-Edge type may have any desired tip or angulation, torque, rotation and in/out values according to well known prescriptions for various systems. Moreover, the configuration of the base may be rhomboidally shaped in the buccal/lingual profile or labia/buccal profile.

As also above noted, the bracket of the invention may optionally include a vertical slot for receiving an uprighting spring or a horizontal tunnel or lumen for receiving an uprighting wire extending through all of the brackets for uprighting all of the teeth in general unison, as disclosed in U.S. Pat. No. 6,682,345. It will be appreciated that the use of the uprighting tunnel or lumen permits mesiodistal uprighting and torquing in connection with the main archwire from the action of the uprighting wire that may be of nickel titanium. Vertical and horizontal control is assured by passive rectangular archwires.

It is understood that the disclosures of the above-identified patents are incorporated by reference in this application.

Further, the bracket of the present invention may be also configured to receive an elastomeric or metal ligature to assist in maintaining the jaws in closed position particularly when a bracket is mounted on a malrotated tooth. Once the tooth is rotated to its proper position, the ligature can be removed on the basis it is no longer needed.

It is therefore an object of the present invention to provide a new and improved self-ligating orthodontic bracket for use in the orthodontic treatment of patients that may be efficiently opened and closed by a professional user for insertion or removal of the main archwire during treatment to enhance the treatment of patients.

Another object of the present invention is in the provision of a self-ligating orthodontic bracket having a pair of jaws openable and closable to accommodate an archwire and which may be configured to be used in the edgewise or Tip-Edge techniques.

A further object of the present invention is to provide a new and improved self-ligating orthodontic bracket that will not only enhance the treatment of patients but also reduce the chair time for the professional user.

Other objects, features and advantages of the invention will be apparent from the following detailed disclosure, taken in conjunction with the accompanying sheets of drawings, wherein like reference numerals refer to like parts.

DESCRIPTION OF THE INVENTION

Referring now to the drawings, and particularly to the embodiment of FIGS. 1-11, for performing the edgewise technique, the bracket 18 includes in general a base 20, a pair of opposed jaw members 22 and 24, a pair of hinge pins 26 and 28, and a spring member 30.

The base member includes a pair of substantially upstanding and substantially parallel hinge members 32 and 34 interconnected at their bottom end by a plate 36. While use of a solid plate is preferred because it defines the mounting face on the lingual of the bracket, it should be appreciated the plate may have openings, or bars may be used to interconnect the hinge members. The hinge members include aligned slots 38 and 40 that are U-shaped and configured to receive a main archwire and thereby coact to define an archwire slot for the bracket. The upstanding members 32 and 34 also include aligned bores 42 and 44 for receiving the hinge pin 28 and aligned bores 46 and 48 for receiving the hinge pin 26.

Figure 10:
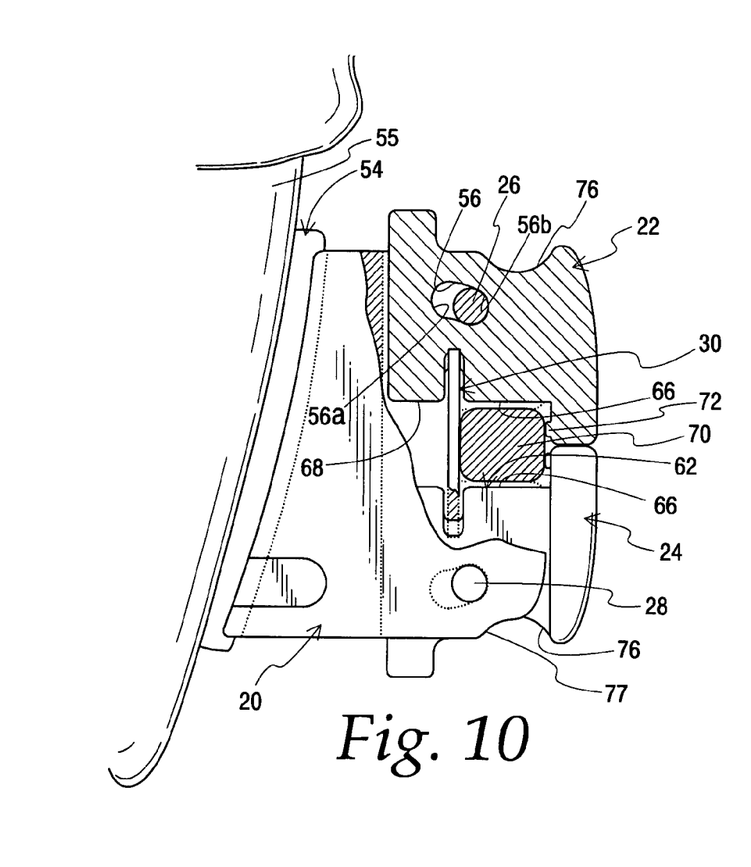
FIG. 10 is a side elevational view of the bracket of FIGS. 1 and 2 mounted on a tooth and using a resin mounting pad, and partially sectional to show underlying parts and the jaws in closed position and an archwire in cross section within the jaws.
Figure 11:
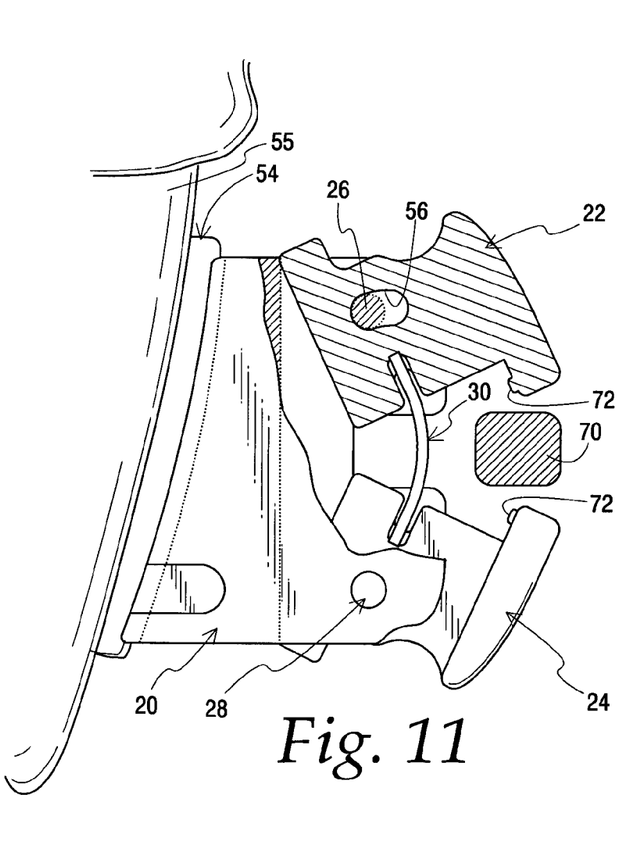
FIG. 11 is a perspective view of the bracket of FIG. 10 but showing the jaws in open position and depicting an archwire in cross section partially removed from the bracket.

The jaw members 22 and 24 are identical to each other and, when mounted on the base, face each other. The base 20 is seen by itself in FIGS. 3-7 and in the exploded view of FIG. 9. As viewed in FIGS. 7 and 9, the plate 36 includes an upper face 50 that is on the side of the base adjacent to the jaws and an underside 52 generally configured to match the surface of the tooth on which it will be mounted. While the surface 52 may be directly bonded to the surface of a tooth, it is preferable that a mounting pad of polymer resin be molded to the mounting side of the base, such as the mounting pad 54 shown in FIGS. 10 and 11. As seen in FIGS. 10 and 11, the bracket through the mounting pad is bonded to a tooth 55. This mounting pad is like that disclosed in U.S. Pat. No. 6,685,468, the disclosure of which is incorporated herein by reference.

The jaws 22 and 24, being substantially identical in shape, are mounted in opposed relation to each other and serve to coact to retain the main archwire in the bracket. The body of each jaw includes a kidney-in-cross-section bore 56 through which a hinge pin extends when the jaw is mounted to the base, as seen in phantom in FIG. 1, and in FIGS. 9 to 11. At the head of each jaw, spaced-apart lugs 58 and 60 are provided and between which a flat surface 62 is disposed that when in cross section in FIG. 10 includes a spring-receiving slot 64 that divides surfaces 66 and 68. The surfaces 66 functions to engage the top and bottom sides of the archwire 70 extending through the bracket and capture the wire when in closed position. Additionally, the lugs 58 and 60 include wire-engaging protrusions 72, as seen in FIGS. 10 and 11, that serve to additionally hold the archwire in place against the spring 30 that serves as a floor to the archwire slot.

Figures 8, 9:
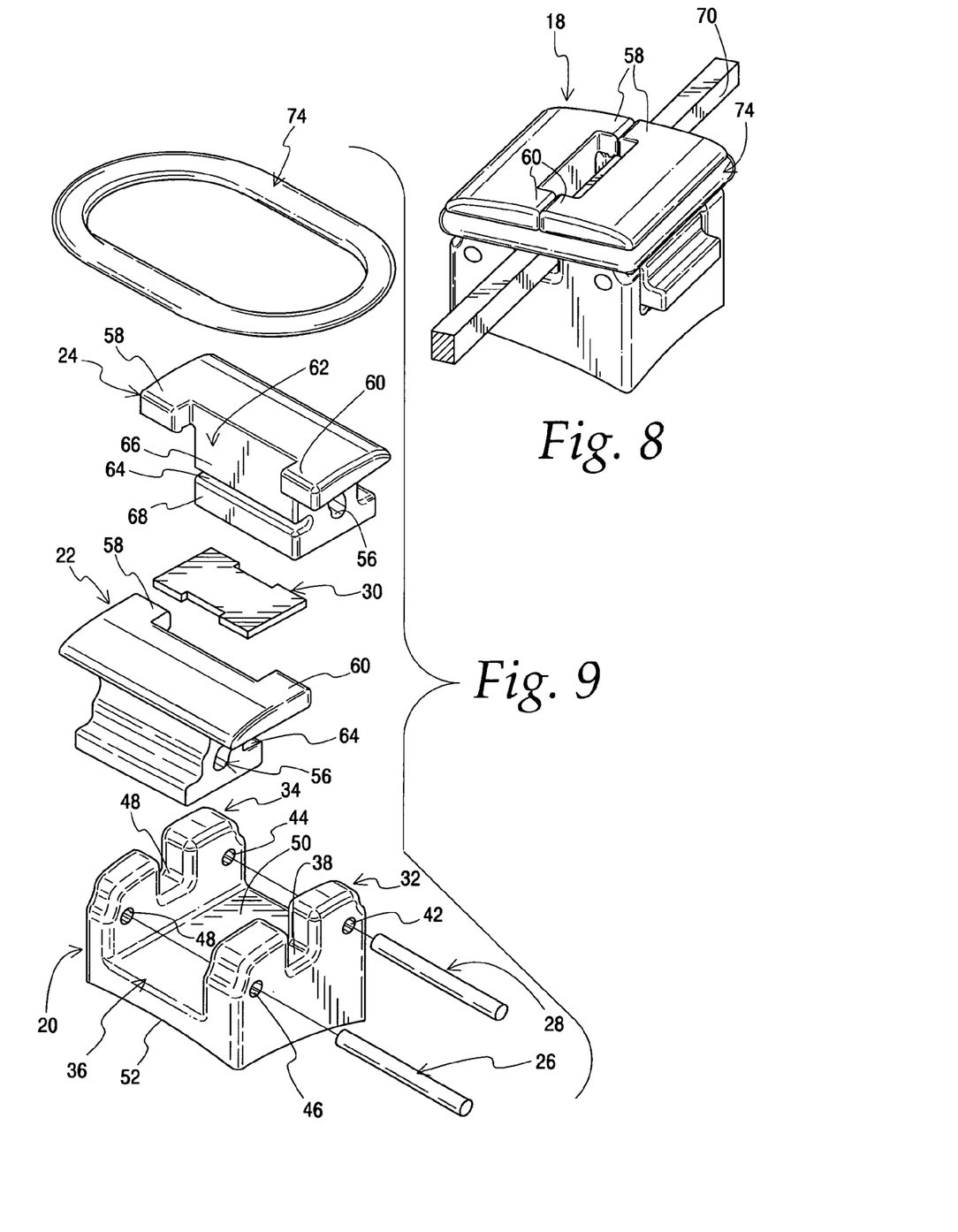
FIG. 8 is a perspective view of the bracket of FIGS. 1 and 2 with the jaws in closed position and showing an archwire in position as well as an optional ligature to assist in holding the jaws in closed position.
FIG. 9 is an exploded view of the bracket of FIGS. 1, 2 and 8 showing the jaws, the base, the spring and hinge pins together with an optional ligature that may be used during a particular phase of treatment.

The spring 30 as seen particularly in FIG. 9 is in the form of a leaf spring and made of a suitable spring material. It will be appreciated that the spring is sized so that it will engage in the slots 64 of each of the jaws, as seen particularly in FIG. 10, so as to control the action of the jaws in unison and selectively hold the jaws in open or closed position.

Figure 1:
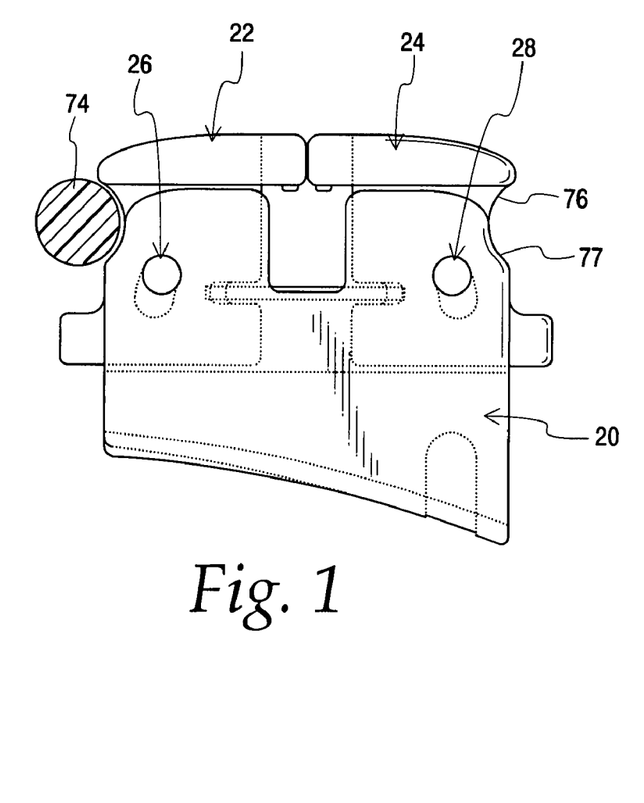
FIG. 1 is a side elevational view of the edgewise version bracket of the present invention showing the jaws in closed position and illustrating in cross section a partial ligature and how it is received by the bracket.
Figure 2:
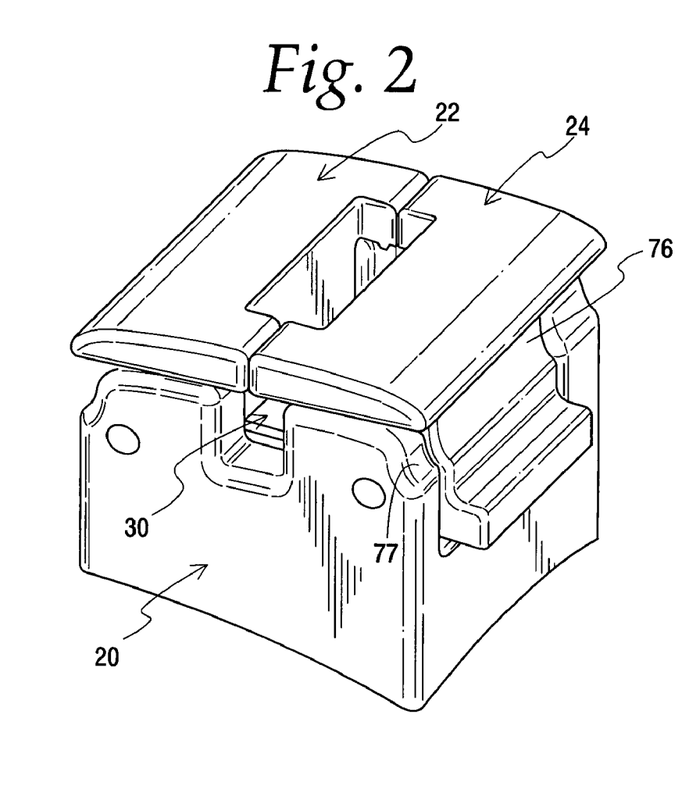
FIG. 2 is a perspective view of the bracket of FIG. 1 also showing the jaws in closed position.
Figure 3:
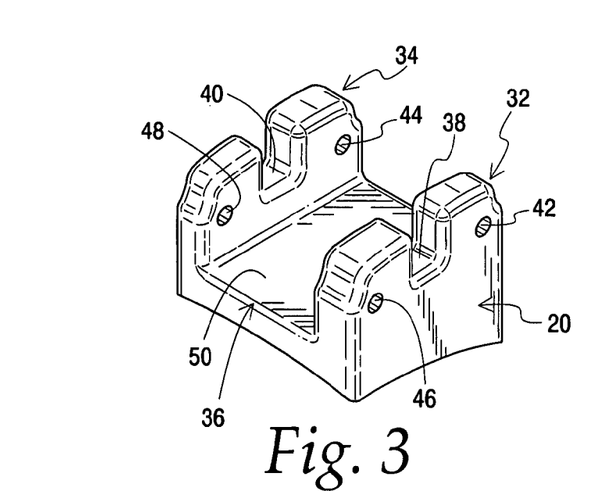
FIG. 3 is a perspective view of the base of the bracket of FIGS. 1 and 2.
Figure 4:
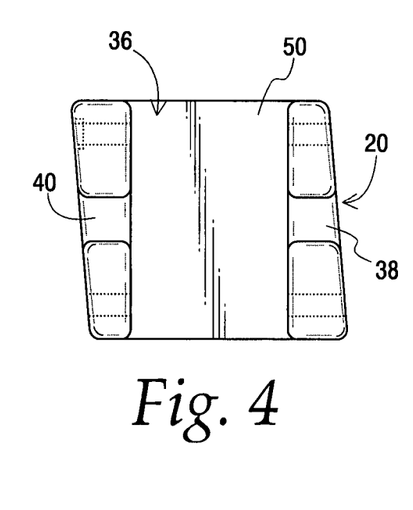
FIG. 4 is a top plan view of the base looking at it from the buccal or labial.
Figure 5:
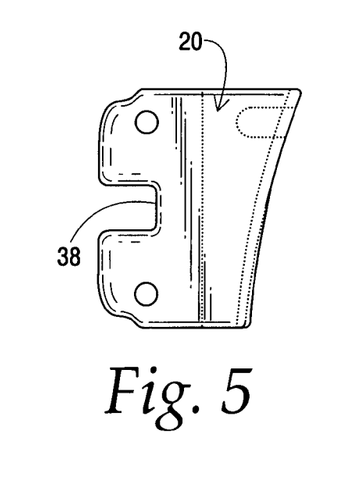
FIG. 5 is a side elevational view of the base viewing it in the vertical.
Figure 6:
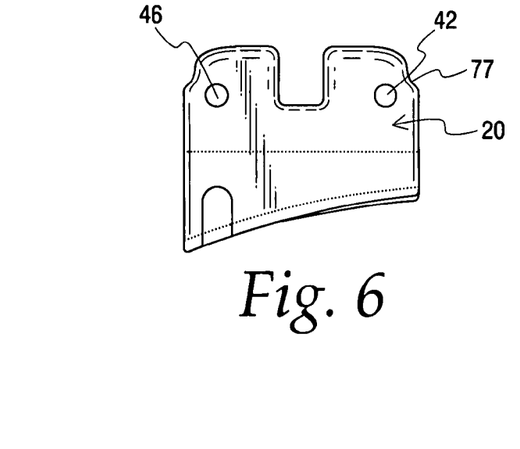
FIG. 6 is a side elevational view of the base viewing it in horizontal position.
Figure 7:
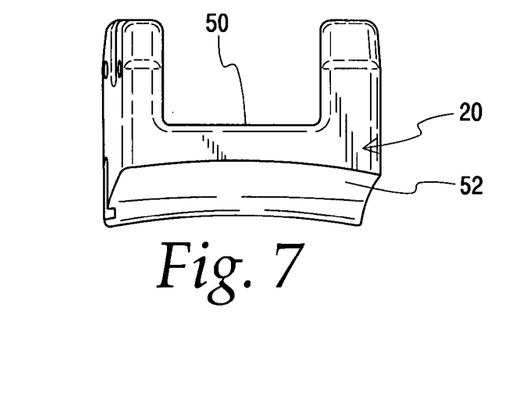
FIG. 7 is a partially perspective and bottom plan view of the base.

As previously set forth, where encountering a badly malrotated tooth, additional forces are needed to maintain the jaws in closed and locked position, and at that time a ligature such as the elastic ligature 74, shown in FIGS. 1 and 9, would be mounted to apply additional closing pressure on the jaws, as seen in FIG. 8. In order to accommodate the positioning of the ligature, the rear of each of the jaws at the head is provided with a partial cylindrical recess 76. Similarly, the corners of the upstanding hinge member 32 and 34 are notched at 77 to facilitate the accommodation of a ligature that is placed onto the bracket, as seen in FIGS. 1, 2, 6, 10 and 11. It will be understood that the cutouts at the engaging sides of the jaws coact as shown in FIG. 8 to reduce the friction between the lugs 58 and 60 of the jaw members. It will be appreciated that while numerical legends are applied to only one of the jaw members as to the specific shape, they will apply to the other jaw member in the same format as the two jaw members are identical to each other but placed in facing relationship to each other.

The spring member 30 shown in FIG. 9 as viewed from above shows slight cutouts at opposite edges along one side, although it may take any desirable shape to provide the desired spring action such that it can engage in and coact with the spring-receiving slots 64 of the jaws. In whatever configuration of the spring that is chosen, it will be understood that it will have the desired spring values to produce the desired interaction between the jaw members and the sliding hinges. While the spring member may be made of any suitable metal spring material, it should be appreciated it could be made of other materials that will provide and produce the necessary spring action for operating the jaws between open and closed locked positions. Similarly, the hinge pins 26 and 28 may be made of metal or a suitable material that would provide the pivotal and slidable hinges of the jaws to function as desired.

In operation, any suitable tool may be used to apply pressure to one or both of the jaws at a desired location to cause them to move to the open position, as shown in FIG. 11, and thereafter to move to the closed position, as shown in FIG. 10. However, closing of the jaws can be accomplished by inserting the archwire within the open jaws against the spring and applying pressure lingually at the mesial and distal sides of the bracket causing the spring to drive the jaws over the hinge pins until the pins engage the lingual or lower ends of the kidney-shaped slots locking the jaws under spring pressure in closed position to lock the archwire to the bracket. By virtue of the kidney-in-cross-section bores 56 of the jaws, the bore or hole 56 may be considered as a cam hole and which includes cam lobes or bumps 56a and 56b, as seen in FIG. 10. A hinge pin 56 is disposed at the top or buccolabial ends 56b of the cam opening when the jaws are in closed position, as shown in FIG. 10, and at the bottom or lingual ends 56a of the cam opening when the jaws are open, as seen in FIG. 11. The angulation of the kidney-shaped bores or openings within the jaws is such that the spring will retain the jaws in closed position, as shown in FIG. 10, or in open position, as shown in FIG. 11. Further, the spring 30 moves away from the base of the bracket during opening of the jaws and toward the base during closing of the jaws, as also described in the above identified U.S. Pat. No. 7,025,591. During opening of the jaws the opening force initially causes the spring to buckle and then the jaws to slide outwardly away from the base as the cam openings in the jaws move overcenter of the hinge pin, and when the hinge pins become aligned with the bottom 56a of the cam openings, the spring 30 causes the jaws to fully open into open and locked position to allow the easy insertion or removal of an archwire. In this position, the spring continues to urge the jaws into open position. When closing the jaws, the forcing of the archwire against the spring causes inward movement of the jaws to the position shown in FIG. 10 which then allows the spring to produce forces to maintain the jaws in closed position. As the jaws are moved between open and closed position, a slight tactile feedback may be felt.

Figures 12, 13:
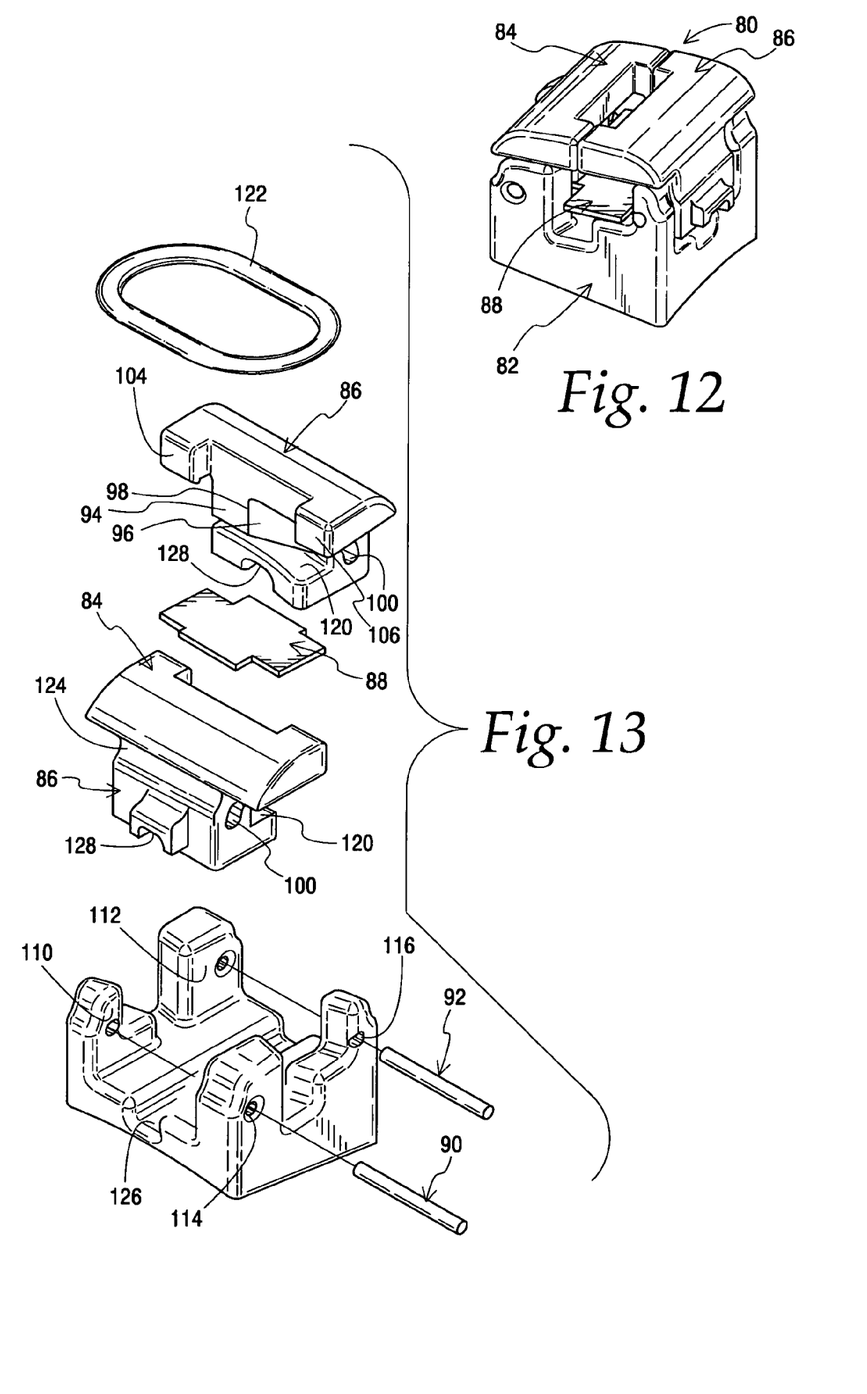
FIG. 12 is a perspective view of a modification of the bracket of the invention and particularly illustrating a bracket having a Tip-Edge archwire slot for performing the Tip-Edge technique.
FIG. 13 is an exploded view of the bracket of FIG. 12 showing the parts in perspective view.

Referring now to FIGS. 12 and 13, a modification is shown where the archwire slot is configured for performing the Tip-Edge technique in that the main archwire slot allows crown tipping, limits root uprighting, and controls torquing, as set forth in U.S. Pat. Nos. 4,877,398; 5,125,832 and 6,682,345. The performance of the Tip-Edge technique which is well known allows tipping and uprighting movements for closing spaces between teeth and in a final stage provides torquing movements. As above mentioned, the disclosures of these patents are also incorporated by reference. Other than to provide a different slot configuration, the operation of this embodiment would be selectively open in locked position for insertion or removal of an archwire or in closed position for retaining and locking an archwire to the bracket, all without the need of having a ligature for maintaining the archwire in the archwire slot as is needed in the brackets in the above prior patents. Thus, the bracket configuration of this embodiment differs from that of the edgewise slot bracket of FIGS. 1-11 essentially in the form of the main archwire slot. However, additionally this embodiment also includes a vertical slot for using an uprighting spring to produce an uprighting function. Such a slot could also be incorporated in the embodiment of FIGS. 1-11. Additionally, this embodiment also is configured so that it can receive a ligature to assist in maintaining the jaws in closed position for treating a patient with a malrotated tooth to prevent escape of the archwire.

This bracket is generally designated by the numeral 80 and includes a base 82, jaws 84 and 86, a spring member 88, and hinge pins 90 and 92.

The jaws 84 and 86 are identical to each other, and each includes stop surfaces 94 and crown tipping surfaces 96 which define a fulcrum 98 between the surfaces. Additionally, each jaw includes a kidney-shaped bore or opening 100 extending mesiodistally through the jaw for receiving a hinge pin, like the embodiment of FIGS. 1-11. At the top of each jaw, a pair of spaced-apart lugs 104 and 106 mate to close the archwire slot. The base of the bracket, generally designated by the numeral 82, serves the same purpose as the base 20 of the embodiment of FIGS. 1-11. The base 82 is provided with upstanding spaced-apart hinge members 110 and 112. Each of the hinge members includes pin openings 114 and 116 for effectively receiving and holding the pins 90, 92 that extend through the kidney-shaped openings in the hinge members 110 and 112. Any suitable hinge pins may be provided that are capable of tightly fitting in the hinge pin openings to lock the jaws to the base. The hinge pins are supported by the openings in the base and extend through kidney-shaped openings of the jaws like in the first embodiment. The spring 88 is similar to but slightly modified in shape from the spring 30 of the first embodiment and is received in slots 120 of the jaws. The spring is configured so that it can serve as the floor of the archwire slot when the jaws are in closed position during any orientation of the bracket on the main archwire.

A ligature 122 may be optionally used to assist in maintaining the jaws in closed position. Preferably, the ligature is elastomeric but it may be made of metal if so desired. At the backside of the jaws is a recess 124 configured such as to receive and maintain in position a ligature during treatment with a patient.

Additionally, this embodiment is configured to receive the tail of an uprighting spring by having a vertically oriented opening formed by a slot or recess 126 in the base and a coacting and mating slot 128 formed in the underside of each of the jaws where the slots 126 and 128 form a vertical opening or slot into which the anchoring end of an uprighting spring may be received. It is well known how an uprighting spring may be mounted on a bracket structure and the main archwire for performing an uprighting function during treatment of a patient.

The spring 88 is configured such that it provides the necessary floor for the main archwire placed in the main archwire slot wherein the opposite ends are depicted in slightly offset relationship to each other so that a sufficient amount of floor is provided for an archwire to be captured in the jaws of the archwire slot configurations at all times.

This embodiment operates substantially the same as the embodiment of FIGS. 1-11 in that the jaws of the bracket are moved to open position for insertion or removal of an archwire or to closed position for retaining the archwire in place on the bracket. The jaws may be opened by any suitable tool engaging and applying pressure at a desired point that will cause opening of the jaws. As in the above embodiment, closing of the jaws can be accomplished by inserting an archwire into the open slot and applying pressure lingually.

Figure 14:
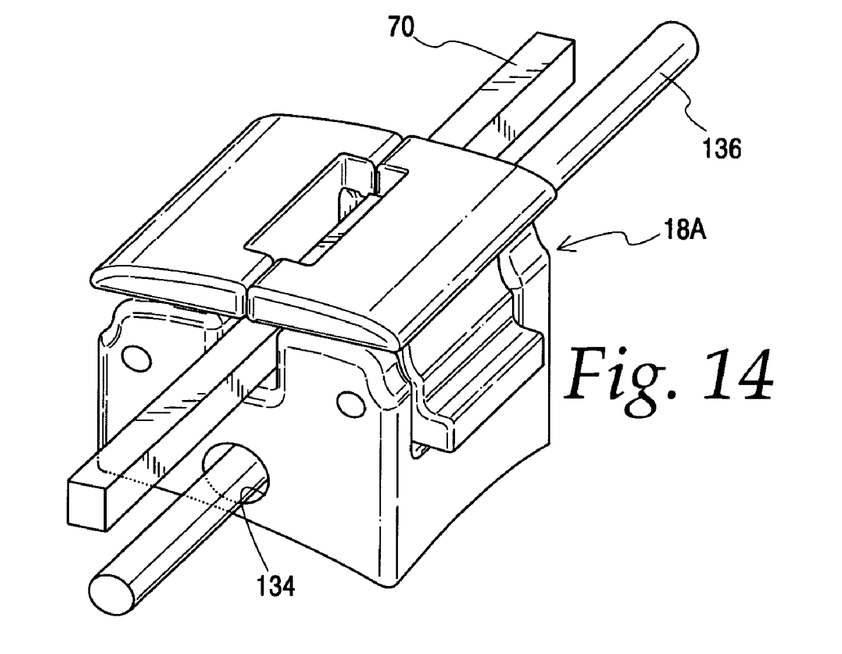
FIG. 14 is a perspective view of a modified bracket for the edgewise technique which additionally shows a tunnel for receiving an uprighting wire and illustrating the main archwire and the uprighting wire in solid.
Figure 15:
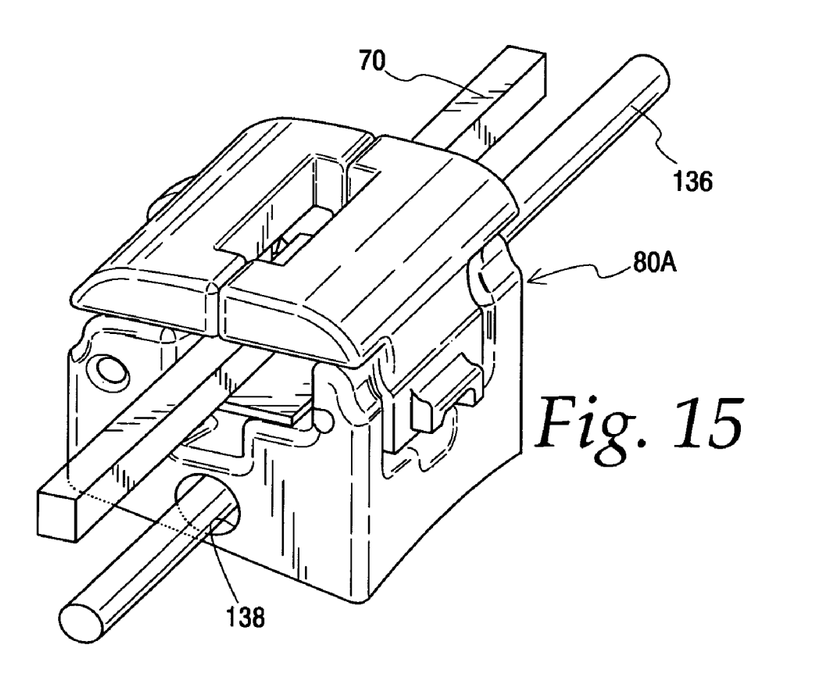
FIG. 15 is a perspective view of the bracket of FIG. 12 capable of performing the Tip-Edge technique and modified to additionally accommodate an uprighting wire.

Modified brackets with an edgewise slot or a Tip-Edge slot are shown in FIGS. 14 and 15 and differ only in that they include tunnels in the base for receiving an uprighting wire like shown in above mentioned U.S. Pat. Nos. 7,264,468 and 6,682,345, respectively.

With respect to the embodiment of FIG. 14, the bracket 18A includes a tunnel 134 provided in the base and substantially in alignment with the main archwire slot and lingual to the main archwire slot for receiving an uprighting wire 136 and functioning as disclosed in U.S. Pat. No. 7,264,468 for producing uprighting functions. Similarly, the bracket 80A of FIG. 15 for performing the Tip-Edge technique includes a mesiodistally extending tunnel 138 for receiving an uprighting wire 136 and functioning as disclosed in U.S. Pat. No. 6,682,345 to produce an uprighting function. Otherwise, the elements of these brackets are the same as in the embodiments of FIGS. 1-13. While the tunnels are shown as cylindrical in shape, it should be appreciated they may be polygonal in shape.

The embodiments of FIGS. 14 and 15, as above mentioned, will operate as to the opening and closing of the jaws in the same manner as the embodiments of FIGS. 1 and 12, respectively.

It will be understood that modifications and variations may be effected without departing from the scope of the novel concepts of the present invention, but it is understood that this application is to be limited only by the scope of the appended claims.

The invention is hereby claimed as follows:

1. A self-ligating orthodontic bracket having an archwire slot for receiving an archwire comprising:
   a base having a single pair of spaced apart and substantially parallel upstanding members having inner ends and outer ends, means interconnecting said members at said inner ends, said members having aligned outwardly projecting slots defining the archwire slot of the bracket and means at said outer ends adjacent said slots for hingedly receiving a pair of jaws,
   said pair of jaws extending between and hingedly connected to said means for hingedly receiving said jaws, said jaws coacting with the archwire slot and being movable between open and closed positions to selectively open the archwire slot for insertion of an archwire into the archwire slot or withdrawal of an archwire from the archwire slot,
   and a spring means engaging said jaws for selectively maintaining said jaws locked in an open or a closed position,
   wherein said spring means additionally defines a floor for said archwire slot between said members.

2. The bracket of claim 1, which further comprises tie wing means for receiving a ligature to further urge said jaws in closed position.

3. The bracket of claim 2, wherein said tie wing means includes a partially concave recess in said jaws coacting with partially concave recesses in said members.

4. The bracket of claim 1, wherein the archwire slot is rectangular in shape such that the bracket can receive a rectangular archwire to perform an edgewise technique.

5. The bracket of claim 4, which further comprises a tunnel in the base for receiving an uprighting wire to perform an uprighting function with other adjacent brackets.

6. The bracket of claim 1, wherein said spring means is in the form of a flat spring engaging slots in said jaws.

7. The bracket of claim 1, which further comprises retention means coacting with said spring means to retain the jaws in open or closed positions.

8. The bracket of claim 7, wherein said retention means includes a kidney-shaped opening in each jaw coacting with a pin anchored at the outer ends of said members.

9. The bracket of claim 8, wherein said kidney-shaped opening defines a cam having adjacent pin-receiving areas separated by a raised portion over which the pins ride when the jaws slide on the pins between the pin-receiving areas, and said spring means applies pressure to maintain the jaws selectively in open or closed positions.

\* \* \* \* \*